United States Patent
Toupin et al.

(10) Patent No.: US 10,762,985 B2
(45) Date of Patent: Sep. 1, 2020

(54) SYSTEM, METHOD, AND NON-TRANSITORY COMPUTER-READABLE STORAGE MEDIA FOR GENERATING ACCOUNTS FOR USE IN COMPUTER SYSTEMS

(71) Applicant: Wal-Mart Stores, Inc., Bentonville, AR (US)

(72) Inventors: Justin Toupin, San Francisco, CA (US); Nathan Thomas Diepenbrock, Highlands Ranch, CO (US)

(73) Assignee: WALMART APOLLO, LLC, Bentonville, AR (US)

( * ) Notice: Subject to any disclaimer, the term of this patent is extended or adjusted under 35 U.S.C. 154(b) by 1132 days.

(21) Appl. No.: 15/009,561

(22) Filed: Jan. 28, 2016

(65) Prior Publication Data
US 2017/0220771 A1    Aug. 3, 2017

(51) Int. Cl.
 *G16H 10/60* (2018.01)
 *G16H 20/00* (2018.01)
 *G16H 20/10* (2018.01)

(52) U.S. Cl.
CPC ............. *G16H 10/60* (2018.01); *G16H 20/00* (2018.01); *G16H 20/10* (2018.01)

(58) Field of Classification Search
CPC ........ G16H 10/60; G16H 20/10; G16H 20/00; G16H 40/20
See application file for complete search history.

(56) References Cited

U.S. PATENT DOCUMENTS

| | | |
|---|---|---|
| 6,543,683 B2 | 4/2003 | Hoffman |
| 6,711,460 B1 | 3/2004 | Reese |
| 6,898,598 B2 | 5/2005 | Himmel et al. |
| 7,487,912 B2 | 2/2009 | Seifert et al. |
| 7,747,695 B1 | 6/2010 | Morris et al. |
| 8,606,698 B2 | 12/2013 | Schultz et al. |
| 9,043,217 B2 | 5/2015 | Cashman et al. |
| 9,195,959 B1 | 11/2015 | Lopez et al. |
| 9,607,345 B1 | 3/2017 | Hendren et al. |
| 2002/0073043 A1 | 6/2002 | Herman et al. |

(Continued)

FOREIGN PATENT DOCUMENTS

| | | | |
|---|---|---|---|
| WO | 2000075834 A2 | 12/2000 | |
| WO | WO-02077758 A2 * | 10/2002 | ............. G06Q 20/26 |

(Continued)

OTHER PUBLICATIONS

Website: www.blueapron.com—BlueApron: Fresh Ingredients, Original Recipes, Delivered to You; downloaded Feb. 3, 2016; 29 pages total. Feb. 3, 2016.

(Continued)

*Primary Examiner* — John P Go
(74) *Attorney, Agent, or Firm* — Bryan Cave Leighton Paisner LLP

(57) ABSTRACT

A system, method, and non-transitory computer-readable storage media programmed to create a pharmacy account based on primary information collected from a new customer when a prescription for purchase of a prescription drug is delivered by the customer, create an on-line account for the new customer based on the pharmacy account for the new customer, and link the pharmacy account and the on-line account together for the new customer.

21 Claims, 14 Drawing Sheets

(56) References Cited

U.S. PATENT DOCUMENTS

| | | |
|---|---|---|
| 2003/0096616 A1 | 5/2003 | Speight et al. |
| 2003/0120607 A1 | 6/2003 | Piotrowski |
| 2003/0187672 A1 | 10/2003 | Gibson |
| 2003/0216950 A1 | 11/2003 | Chen |
| 2004/0204954 A1 | 10/2004 | Lacko |
| 2004/0236635 A1 | 11/2004 | Publicover |
| 2005/0165651 A1 | 7/2005 | Mohan |
| 2007/0088624 A1 | 4/2007 | Vaughn et al. |
| 2007/0124170 A1 | 5/2007 | Cabell et al. |
| 2007/0150375 A1 | 6/2007 | Yang |
| 2007/0204169 A1 | 8/2007 | Bahl et al. |
| 2007/0226071 A1 | 9/2007 | Kern et al. |
| 2008/0133283 A1 | 6/2008 | Backer et al. |
| 2009/0076875 A1 | 3/2009 | Lert, Jr. et al. |
| 2009/0181131 A1 | 7/2009 | Forbes-Roberts |
| 2009/0271265 A1 | 10/2009 | Lay et al. |
| 2010/0121807 A1 | 5/2010 | Perrier et al. |
| 2011/0016007 A1 | 1/2011 | Shiftan et al. |
| 2011/0125519 A1 | 5/2011 | Dhoble |
| 2011/0231272 A1 | 9/2011 | Englund et al. |
| 2011/0307265 A1 | 12/2011 | Bannis |
| 2011/0307547 A1 | 12/2011 | Backer et al. |
| 2011/0313790 A1 | 12/2011 | Yao |
| 2011/0321127 A1 | 12/2011 | Pitroda et al. |
| 2012/0072311 A1 | 3/2012 | Khan |
| 2012/0078673 A1 | 3/2012 | Koke et al. |
| 2012/0084391 A1 | 4/2012 | Patel et al. |
| 2012/0114116 A1 | 5/2012 | Sulaiman et al. |
| 2012/0123674 A1 | 5/2012 | Perks et al. |
| 2012/0166298 A1 | 6/2012 | Smith et al. |
| 2012/0191573 A1 | 7/2012 | Miller |
| 2012/0221446 A1 | 8/2012 | Grigg et al. |
| 2012/0253828 A1* | 10/2012 | Bellacicco, Jr. ... G06Q 30/0201 705/1.1 |
| 2012/0290609 A1 | 11/2012 | Britt |
| 2013/0151268 A1* | 6/2013 | Fletcher ............... G06Q 50/22 705/2 |
| 2013/0159858 A1 | 6/2013 | Joffray et al. |
| 2013/0173403 A1 | 7/2013 | Grigg et al. |
| 2013/0179180 A1 | 7/2013 | Patra |
| 2013/0196297 A1 | 8/2013 | Anwar |
| 2013/0224694 A1 | 8/2013 | Moore et al. |
| 2013/0290145 A1 | 10/2013 | Durst, Jr. |
| 2014/0080102 A1 | 3/2014 | Krishna |
| 2014/0149139 A1* | 5/2014 | Bowen, Jr. ............ G06Q 50/24 705/3 |
| 2014/0156297 A1 | 6/2014 | Schaefer et al. |
| 2014/0188648 A1 | 7/2014 | Argue et al. |
| 2014/0222482 A1 | 8/2014 | Gautam et al. |
| 2014/0244296 A1 | 8/2014 | Linn et al. |
| 2014/0258022 A1 | 9/2014 | Zamer et al. |
| 2014/0278520 A1* | 9/2014 | Abuzeni ............... G06Q 50/22 705/2 |
| 2014/0279269 A1 | 9/2014 | Brantley et al. |
| 2014/0344109 A1* | 11/2014 | Prindle ............. G06Q 30/0633 705/26.8 |
| 2015/0161353 A1 | 6/2015 | Emerson |
| 2015/0242592 A1 | 8/2015 | Weiss et al. |
| 2015/0261934 A1 | 9/2015 | Miller |
| 2015/0285775 A1 | 10/2015 | Gurumohan et al. |
| 2015/0294084 A1 | 10/2015 | McCauley et al. |
| 2015/0294387 A1 | 10/2015 | Karmazyn et al. |
| 2016/0205180 A1 | 7/2016 | Jan et al. |
| 2016/0364547 A1 | 12/2016 | Love et al. |
| 2017/0091424 A1* | 3/2017 | Haigh ................. G06F 19/3475 |
| 2017/0213271 A1 | 7/2017 | Nelms et al. |
| 2017/0220649 A1 | 8/2017 | Toupin |
| 2017/0220684 A1 | 8/2017 | Toupin et al. |
| 2017/0220741 A1 | 8/2017 | Toupin et al. |
| 2017/0220761 A1 | 8/2017 | Toupin et al. |
| 2017/0220762 A1 | 8/2017 | Toupin et al. |
| 2017/0220763 A1 | 8/2017 | Toupin et al. |
| 2017/0220764 A1 | 8/2017 | Toupin et al. |
| 2017/0220765 A1 | 8/2017 | Toupin et al. |
| 2017/0220770 A1 | 8/2017 | Toupin et al. |
| 2017/0221123 A1 | 8/2017 | Toupin |
| 2017/0221129 A1 | 8/2017 | Toupin |
| 2017/0242976 A1 | 8/2017 | Howieson et al. |
| 2018/0130548 A1 | 5/2018 | Fisher |

FOREIGN PATENT DOCUMENTS

| | | |
|---|---|---|
| WO | 2007134378 A1 | 11/2007 |
| WO | 2012064026 A2 | 5/2012 |

OTHER PUBLICATIONS

Utility U.S. Appl. No. 15/009,327, filed Jan. 28, 2016 Entitled "System, Method, and Non-Transitory Computer-Readable Storage Media for Displaying Information on Mobile Devices".

Utility U.S. Appl. No. 15/009,374, filed Jan. 28, 2016 Entitled "System, Method, and Non-Transitory Computer-Readable Storage Media for Evaluating Search Engine Results and Displaying a Virtual Pill Case".

Utility U.S. Appl. No. 15/009,417, filed Jan. 28, 2016 Entitled "System, Method, and Non-Transitory Computer-Readable Storage Media for Generating Data for Use in Computer Systems".

Utility U.S. Appl. No. 15/009,436, filed Jan. 28, 2016 Entitled "System, Method, and Non-Transitory Computer-Readable Storage Media for Generating Data for Use in Computer Systems".

Utility U.S. Appl. No. 15/009,654, filed Jan. 28, 2016 Entitled "System, Method, and Non-Transitory Computer-Readable Storage Media for Creating a Meal Plan".

Utility U.S. Appl. No. 15/009,583, filed Jan. 28, 2016 Entitled "System, Method, and Non-Transitory Computer-Readable Storage Media for Secure Discrete Communication With Pharmacist of Retail Store".

Utility U.S. Appl. No. 15/009,454, filed Jan. 28, 2016 Entitled "System, Method, and Non-Transitory Computer-Readable Storage Media for Generating Data for Use in Computer Systems".

Utility U.S. Appl. No. 15/009,598, filed Jan. 28, 2016 Entitled "System, Method, and Non-Transitory Computer-Readable Storage Media for Endless Aisle of Products in Retail Store".

Utility U.S. Appl. No. 15/009,611, filed Jan. 28, 2016 Entitled "System, Method, and Non-Transitory Computer-Readable Storage Media for Mobile Check-In in Retail Store".

Utility U.S. Appl. No. 15/009,634, filed Jan. 28, 2016 Entitled "System, Method, and Non-Transitory Computer-Readable Storage Media for Mobile Check-Out in Retail Store".

Utility U.S. Appl. No. 15/009,644, filed Jan. 28, 2016 Entitled "System, Method, and Non-Transitory Computer-Readable Storage Media for Evaluating Search Results in a Customer Queueing System".

* cited by examiner

| Pharmacy User ID | Drug ID | Description | Dosage | No. of Refills | Refill Frequency | Last Refill | Mobile Device ID/ Messaging API |
|---|---|---|---|---|---|---|---|
| Alice011 | Drug001 | Albuterol, Bronchodilator | 200 mcg | 2 | Monthly | 09/08/15 | MD002; androidAPI01 |
| Alice011 | Drug005 | Antihistamines | 25mg | 12 | bi-monthly | 12/01/14 | MD002; androidAPI01 |
| Amy003 | Drug012 | Captopril, Ace Inhibitor | 12.5mg | 5 | Yearly | 05/16/15 | MD025; androidAPI01 |
| Carl004 | Drug020 | Digoxin, Glycosides | 750 mcg | 2 | monthly | 06/05/15 | MD0062; iPhoneAPI002 |

FIG. 4

SYSTEM, METHOD, AND NON-TRANSITORY COMPUTER-READABLE STORAGE MEDIA FOR GENERATING ACCOUNTS FOR USE IN COMPUTER SYSTEMS

COPYRIGHT NOTICE

The figures included herein contain material that is subject to copyright protection. The copyright owner has no objection to the facsimile reproduction by anyone of this patent document as it appears in the U.S. Patent and Trademark Office, patent file or records, but reserves all copyrights whatsoever in the subject matter presented herein.

BACKGROUND OF THE INVENTION

1. Field of the Invention

U.S. Patent Classification Primary Class: 707 (DATA PROCESSING: DATABASE, DATA MINING, AND FILE MANAGEMENT OR DATA STRUCTURES). Art Unit: 2161.

The present invention relates to online transactional processing for account generation, and more particularly, to systems, methods, and non-transitory computer-readable storage media that generate accounts for pharmacy customers of a retail store of a retailer.

2. Description of the Related Art

Many pharmacy consumers desire to obtain services related to their general heath and the pharmaceutical medications being prescribed to them remotely, e.g., on-line, through the Internet, or using a specially designed application or app on a personal computer or mobile device, such as a tablet or cell phone. In addition, pharmacy customers desire to have an account that facilitates their purchase of prescription drugs and an account for purchase of general items from a retail store of a retailer.

When a customer goes to a pharmacy of a retail store to get a prescription filled, a pharmacy account is created. When the same customer creates a digital or on-line account, the customer has to link the on-line account with the pharmacy account. As such, users may become frustrated with having to link these accounts together. Many pharmacy consumers are prescribed multiple medications to take daily, particularly those who are elderly and/or those suffering from chronic medical conditions. Such consumers often have problems adhering to a medication schedule. Non-adherence to a medication schedule may have a variety of causes, including the patient forgetting to take a dose, failing to timely refill a prescription, or misunderstanding dosing instructions. Failure to adhere to a medication schedule as prescribed results in missed doses of medication(s), resulting in lower efficacy or inefficacy of medications, which may cause adverse health effects and even death. In addition, medication non-adherence may lead to increased health care costs over time.

Many pharmacy consumers desire to obtain information related to the pharmaceutical medications being prescribed to them remotely, e.g., on-line, through the Internet, or using a specially designed application or app on a personal computer or mobile device, such as a tablet or cell phone. At least some known web hosting systems include information associated with pharmaceutical drugs including treated illnesses and potential side effects. However, many of the systems do not address medication adherence issues, nor do they provide personalized information about prescribed medications.

It is, therefore, desirable to provide a new system, method, and non-transitory computer-readable storage media that allows for generating accounts for a retail store. It is also desirable to provide a new system, method, and non-transitory computer-readable storage media that allows a customer to generate a pharmacy account and an on-line account automatically. It is further desirable to provide a new system, method, and non-transitory computer-readable storage media that automatically links a pharmacy account and an on-line account together by providing an e-mail address of the customer. Thus, there is a need in the art to provide a system, method, and non-transitory computer-readable storage media for generating accounts for a retail store that meets at least one of these desires.

SUMMARY OF THE INVENTION

In different embodiments of the present invention, systems, methods, and non-transitory computer-readable storage media are provided for generating, communicating, and displaying information to users via mobile computing devices.

In one embodiment of the present invention, a system includes a server including a processor programmed to create a pharmacy account based on primary information collected from a new customer when a prescription for purchase of a prescription drug is delivered by the customer. The processor is also programmed to create an on-line account for the new customer based on the pharmacy account for the new customer. The processor is further programmed to link the pharmacy account and the on-line account together for the new customer.

In another embodiment of the present invention, a computer-implemented method including the steps of creating a pharmacy account based on primary information collected from a new customer when a prescription for purchase of a prescription drug is delivered by the customer. The method also includes the steps of creating an on-line account for the new customer based on the pharmacy account for the new customer. The method further includes the steps of linking the pharmacy account and the on-line account together for the new customer.

In yet another embodiment, one or more non-transitory computer-readable storage media, having computer-executable instructions embodied thereon are provided. When executed by at least one processor, the computer-executable instructions cause the processor to create a pharmacy account based on primary information collected from a new customer when a prescription for purchase of a prescription drug is delivered by the customer. The computer-executable instructions also cause the processor to create an on-line account for the new customer based on the pharmacy account for the new customer. The computer-executable instructions further cause the processor to link the pharmacy account and the on-line account together for the new customer.

One advantage of the present invention is that a new system, method, and non-transitory computer-readable storage media is provided for generating accounts for a pharmacy customer of a retail store. Another advantage of the present invention is that the system, method, and non-transitory computer-readable storage media allows a customer to generate a pharmacy account and automatically generate a digital or on-line account. Yet another advantage of the present invention is that the system, method, and non-transitory computer-readable storage media automatically links the on-line account and the pharmacy account together when the pharmacy account is created. Still another advantage of the present invention is that the system, method, and non-transitory computer-readable storage media uses only one login and password to allow the pharmacy customer to access both (linked) accounts. A further advantage of the present invention is that the system, method, and non-transitory computer-readable storage media allows a pharmacy customer to use their e-mail address, if they already have an online account, to automatically link their pharmacy account and a digital or on-line account together.

Other features and advantages of the present invention will be readily appreciated, as the same becomes better understood, after reading the subsequent description taken in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 4 is an illustration of exemplary database records generated by the system of FIG. 1, according to embodiments of the present invention.

Figure 1:
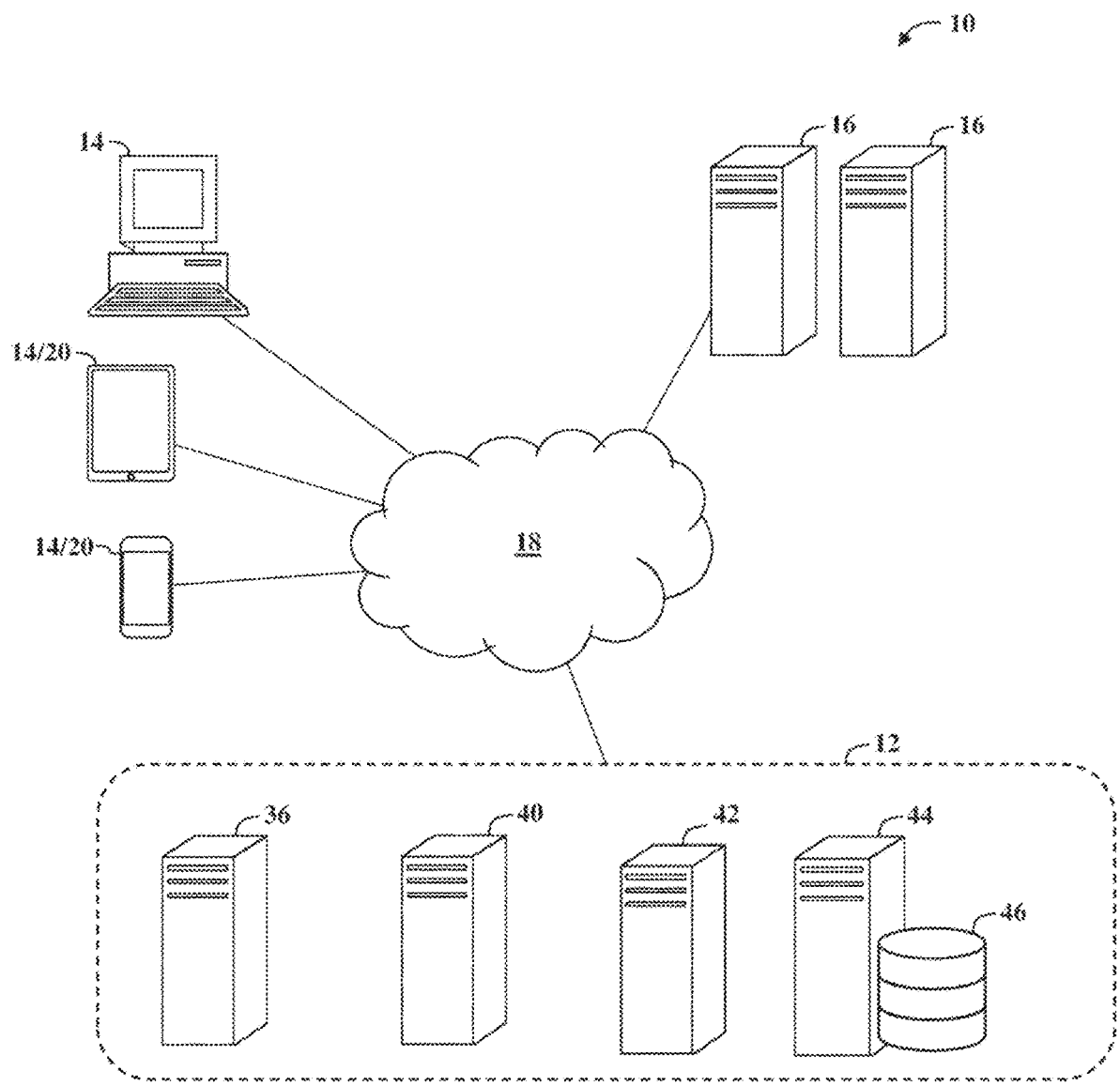
FIG. 1 is a schematic illustrating various aspects of a system, according to the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION OF THE PREFERRED EMBODIMENT(S)

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, system, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis. The term "coupled" means any suitable communications link, including but not limited to the Internet, a LAN, a cellular network, or any suitable communications link. The communications link may include one or more of a wired and wireless connection and may be always connected, connected on a periodic basis, and/or connected on an as needed basis.

With reference to the FIGS. and in operation, the present invention provides a networked computer system 10, method, and computer product media that generates accounts for pharmacy customers. Referring to FIG. 1, an exemplary environment in which the networked computer system 10 operates is illustrated. In general, the present invention describes a networked computer system 10 that generates pharmacy accounts and generates and digital accounts or an on-line accounts for pharmacy customers.

For clarity in discussing the various functions of the system 10, multiple computers and/or servers are discussed as performing different functions. These different computers (or servers) may, however, be implemented in multiple different ways such as modules within a single computer, as nodes of a computer system, etc. . . . . The functions performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

In the illustrated embodiment, the system 10 includes a server system 12 that is coupled in communication with one or more user computing devices 14 and one or more $3^{rd}$ party entity server systems 16 via a communications network 18. The communications network 18 may be any suitable connection, including the Internet, file transfer protocol (FTP), an Intranet, LAN, a virtual private network (VPN), cellular networks, etc. . . . , and may utilize any suitable or combination of technologies including, but not limited to wired and wireless connections, always on connections, connections made periodically, and connections made as needed.

The user computing device 14 may include any suitable device that enables a user to access and communicate with the system 10 including sending and/or receiving information to and from the system 10 and displaying information received from the system 10 to a user. For example, in one embodiment, the user computing device 14 may include, but is not limited to, a desktop computer, a laptop or notebook computer, a tablet computer, smartphone/tablet computer hybrid, a personal data assistant, a handheld mobile device including a cellular telephone, and the like. The user computing device 14, as well as any other connected computer systems and their components included in the system 10, can create message related data and exchange message related data (e.g., near field communication ("NFC") payloads, Bluetooth packets, Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the communications network 18.

Figure 3:
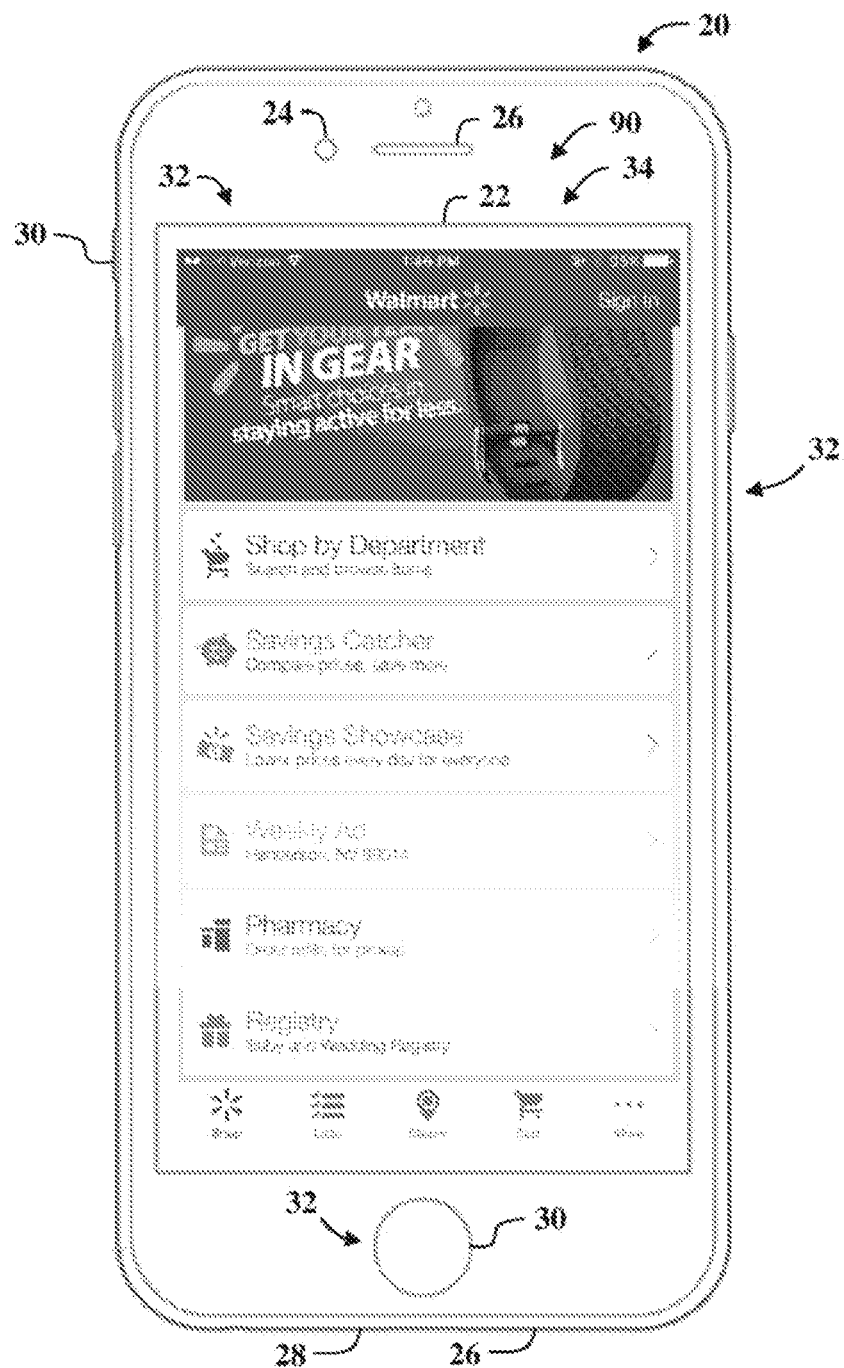
FIG. 3 is an illustration of an exemplary screenshot from the system of FIG. 1, according to an embodiment of the present invention.

In one embodiment, the user computing device includes a mobile computing device 20 (shown in FIG. 3) such as, for example, a smartphone such as an iPhone'. The mobile computing device 20 includes a processor coupled to a memory device, and a database for storing various programs and data for use in operating the mobile computing device 20. The mobile computing device 20 may also include a touchscreen display device 22, one or more video image cameras 24, one or more speakers 26, a microphone 28, at least one input button 30, and one or more sensors 32 including, but not limited to, a touch ID fingerprint sensor coupled to an input button 30, a barometer, a three-axis gyro, an accelerometer, proximity sensor, and an ambient light sensor. In addition, the mobile computing device 20 may also include a Wi-Fi antenna, a cellular network antenna, a Bluetooth™ communications device, assisted GPS and GLONASS, a digital compass, and an iBeacon microlocation device.

In the illustrated embodiment, the mobile computing device 20 includes a web browser program stored in the memory device. The processor executes the web browser program to display web pages on the touchscreen display device 22 that includes information received from the server system 12 to enable a user to interact with and operate the server system 12. In addition, the mobile computing device 20 may be programmed to store and execute a computer program applications that display user interfaces 34 (shown in FIGS. 3 and 6-9) on the touchscreen display device 22 that allows the user to access the server system 12 to retrieve and store information within the server system 12 as well as interact with and operate the server system 12. In addition, in one embodiment, the system 10 may install one or more mobile computer application programs in the memory device of the mobile computing device 20. When initiated by the processor of the mobile computing device 20, the mobile computer application program causes the processor of the mobile computing device 20 to perform some or all of the functions of the server system 12.

In the illustrated embodiment, the $3^{rd}$ party entity server systems 16 are associated with service entities that provide goods and/or services to pharmacy customers. The server system 12 is programmed to communicate with the $3^{rd}$ party entity server systems 16 to transmit and receive information associated with pharmacy customers to enable the $3^{rd}$ party entity server systems 16 to provide additional services to the pharmacy customers. For example, in one embodiment, the 3rd party entity server systems 16 may be associated with organizations and/or companies that provide healthcare services to consumers such as, for example, health insurance companies, medical providers, healthcare professionals, hospitals, medical care facilities, healthcare monitoring entities, consumer product companies, consumer retail establishments, and the like. In addition, in some embodiments, the 3rd party entity server systems 16 may be associated with systems supporting mobile computer application programs being stored on the mobile computing devices 20 associated with pharmacy customers.

In the illustrated embodiment of FIG. 1, the server system 12 includes a website hosting server 36, a pharmacy account server 40, a digital account or on-line account server 42, a database server 44, and a database 46. The database server 44 includes a memory device that is connected to the database 46 to retrieve and store information contained in the database 46. The database 46 contains information on a variety of matters, such as, for example, web pages associated with one or more websites, search queries, pharmaceutical drug information, refill information, entity authentication information, customer pharmacy account information, product records, notification messages, mobile device identifies, mobile device application program interfaces (APIs), and/or any suitable information that enables the system 10 to function as described herein. In one embodiment, some or all of the information contained in the database 46 may also be stored in the database of the mobile computing device 20.

In the illustrated embodiment, the database 46 includes a pharmacy account list 48 (shown in FIG. 4) that includes a plurality of user pharmacy account records 50. Each user pharmacy account record 50 is associated with a corresponding pharmacy customer and includes user identification information 52 associated with the pharmacy customer and pharmaceutical drug data associated with pharmaceutical drugs prescribed to and/or purchased by the corresponding pharmacy customer. The user identification information 52 includes user identifying data such as, for example, a unique user ID and/or password. The user identification information 52 may also include user contact information such as, for example, a phone number, an email, and/or a mobile device data 54 associated with a mobile computing device 20 associated with the corresponding pharmacy customer. For example, the mobile device data 54 may include, but is not limited to, a unique mobile device ID, operating system, phone number, IP address, mobile device API, and/or any suitable information that enables the system 10 to communicate with the corresponding mobile computing device 20.

In the illustrated embodiment, the database 46 includes a digital or on-line account list that includes a plurality of user on-line account records. Each user on-line account record is associated with a corresponding on-line customer and includes user identification information associated with the on-line customer and product data associated with products ordered and/or purchased wither on-line or in one or more retail stores by the corresponding on-line customer. The user identification information includes user identifying data such as, for example, a unique user ID and/or password. The user identification information may also include user contact information such as, for example, a phone number, an email, and/or a mobile device data associated with a mobile computing device 20 associated with the corresponding on-line customer. For example, the mobile device data may include, but is not limited to, a unique mobile device ID, operating system, phone number, IP address, mobile device API, and/or any suitable information that enables the system 10 to communicate with the corresponding mobile computing device 20. It should be appreciated that the on-line account record is similar to the pharmacy account record 50.

In the illustrated embodiment, each user pharmacy account record 50 includes a plurality of data categories 56 associated with the pharmaceutical drugs prescribed to and/or purchase by the pharmacy customer. The data categories 56 includes information associated with the pharmaceutical drugs and activities associated with the pharmacy customers. For example, in one embodiment, each user pharmacy account record 50 may include a first data group 58 including data categories 56 including information associated with a corresponding pharmaceutical drug and a second data group 60 including data categories including information indicating pharmacy customer activities associated with the corresponding pharmaceutical drug. The first data group 58 may include data categories 56 including information indicating a unique drug ID associated with the pharmaceutical drug, pharmaceutical drug description, drug category, prescribed use information, dosage information, and/or any suitable information associated with the corresponding pharmaceutical drug. The second data group 60 may include data categories 56 including information indicating a number of refills remaining, a refill frequency, a date and/or time of the last refill purchase, purchase date, and/or prescription expiration, and/or any suitable information associated with pharmacy customer activity.

Figure 5:
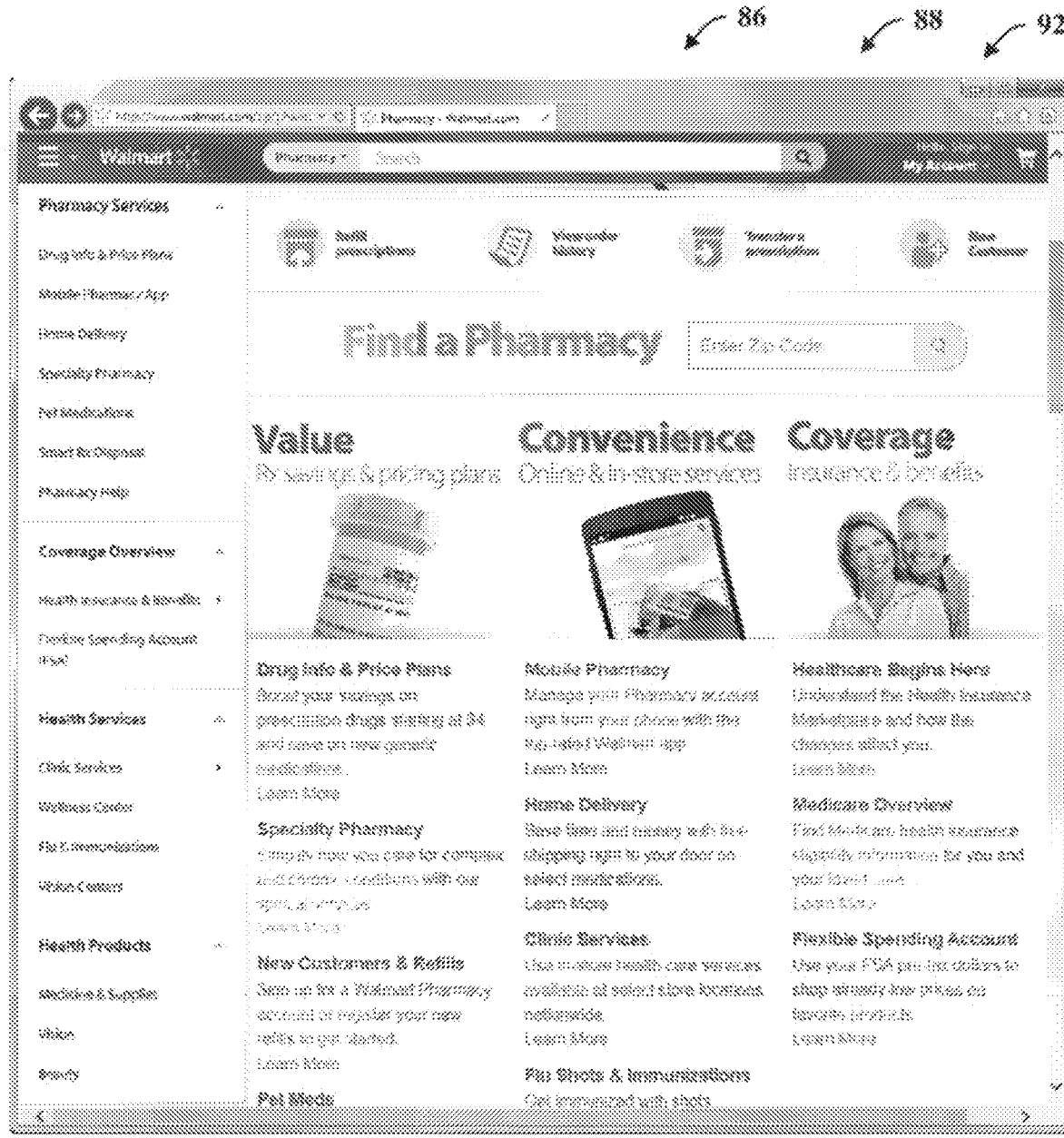
FIG. 5 is an illustration of an exemplary screenshot from the system of FIG. 1, according to an embodiment of the present invention.

The website hosting server 36 is configured to host a website 86 that is accessible by a user via one or more user computing devices 14. The website hosting server 36 retrieves and stores web pages 88 (shown in FIG. 5) associated with one or more websites 86 in response to requests received by the user via the user computing device 14 to allow users to interact with the website and search and/or purchase products such as, for example, goods and/or services via the web site. In one embodiment, the website hosting server 36 is configured to generate and display web pages 88 associated with the website in response to requests being received from consumers or customers via corresponding web browsers that are displayed on the user computing devices 14. In addition, the website hosting server 36 may be configured to generate and display a mobile webpage 90 (shown in FIGS. 3 and 6-9) that is displayed on one or more mobile computing devices 20. For example, in one embodiment, the website hosting server 36 may display a pharmacy webpage 92 (shown in FIGS. 6-9) in response to receiving a user request that allows a user to access a corresponding user pharmacy account record 50, input product search requests including search criteria including one or more search terms, purchase pharmaceutical drugs, request prescription refills, request pharmacist consultations, schedule pharmacy and/or medical clinic appointments, and the like. In addition, the website hosting server 36 may be configured to generate and display a mobile webpage for the in-store on-line webpage that is displayed on one or more mobile computing devices 20. For example, in one embodiment, the website hosting server 36 may display an in-store on-line webpage (similar to that shown in FIGS. 6-9) in response to receiving a user request that allows a user to access a corresponding user in-store on-line account record, input product search requests including search criteria including one or more search terms, purchase products, request product information, and the like.

The website hosting server 36 may allow customers to login and access corresponding customer pharmacy accounts including account information such as, for example, previous purchases, pending proscription orders, pending medication refills, and/or pharmaceutical drug information. For example, the website hosting server 36 may display a login page 94 (shown in FIGS. 7-8), receive a unique customer ID such as, for example, a username and/or password, and identify the customer account associated with the unique customer ID to enable the identified customer to access information and/or features associated with the corresponding customer pharmacy account.

The website hosting server 36 may allow customers to login and access corresponding customer in-store on-line accounts including account information such as, for example, previous purchases, pending product orders, pending product purchases, etc. For example, the website hosting server 36 may display a login page (similar to that shown in FIGS. 7-8), receive a unique customer ID such as, for example, a username and/or password, and identify the customer account associated with the unique customer ID to enable the identified customer to access information and/or features associated with the corresponding customer in-store on-line account.

In the illustrated embodiment, the pharmacy account server 40 is programmed to monitor activities of pharmacy customers including the purchase and use of prescription pharmaceutical medications, to generate and store pharmacy records associated with the pharmacy customer activities, and to receive and transmit information to one or more $3^{rd}$ party entity server system 16. For example, in one embodiment, the pharmacy account server 40 may provide pharmacy customer information to an entity server system 16 for use in providing value-added services to the pharmacy customer such as, for example, health monitoring services, health insurance services, medication adherence services, consumer products, health education services, and/or any suitable services that may use information being generated by the pharmacy account server 40.

In one embodiment, the pharmacy account server 40 may also access the user pharmacy account record 50 associated with the user ID, retrieve contact information associated with the corresponding pharmacy customer, and transmit a verification message to the pharmacy customer based on the retrieved contact information. The verification message may include a verification hyperlink including verification data that allows the pharmacy customer to access the hyperlink and transmit a verification signal to the pharmacy account server 40. For example, in one embodiment, the user pharmacy account record 50 may include an email address and/or a phone number associated with a phone capable of received SMS text messages. The pharmacy account server 40 may generate the verification message including an email message and/or SMS text message and transmit the email message and/or SMS text message including the verification hyperlink to the pharmacy customer.

The digital account or on-line account server 42 is programmed to monitor activities of customers including the purchase of products either on-line or in one or more retail stores, to generate and store product purchase records associated with the customer activities, and to receive and transmit information to one or more $3^{rd}$ party entity server system 16. For example, in one embodiment, the on-line account server 42 may provide customer information to an entity server system 16 for use in providing value-added services and/or products to the customer such as, for example, product insurance, product warranties, etc. and/or any suitable services that may use information being generated by the on-line account server 42.

Figure 2:
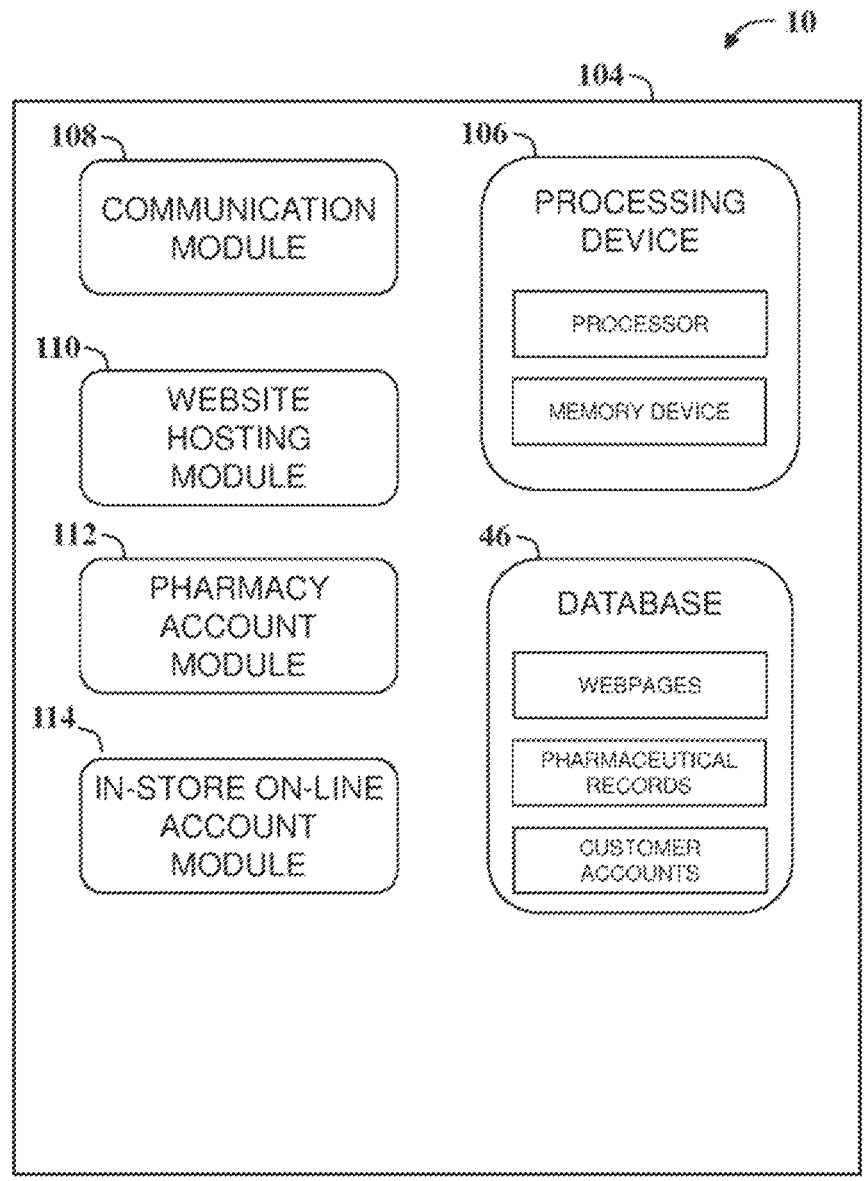
FIG. 2 is a schematic illustrating example components of a server computer that may be used with the system shown in FIG. 1, according to an embodiment of the present invention.

Referring to FIG. 2, in one embodiment, the system 10 may include a system server 104 that is configured to perform the functions of the website hosting server 36, the pharmacy account server 40, the on-line account server 42, and the database server 44. In the illustrated embodiment, the system server 104 includes a processing device 106 and the database 46.

The processing device 106 executes various programs, and thereby controls components of the system server 104 according to user instructions received from the user computing device 14. The processing device 106 may include memory, e.g., read only memory (ROM) and random access memory (RAM), storing processor-executable instructions and one or more processors that execute the processor-executable instructions. In embodiments where the processing device 106 includes two or more processors, the processors can operate in a parallel or distributed manner. In an example, the processing device 106 may execute a communications module 108, a website hosting module 110, a pharmacy account module 112, and an on-line account module 114.

The processing device 106 may also include a memory device for storing programs and information in the database 46, and retrieving information from the database 46 that is used by the processor to perform various functions described herein. The memory device may include, but is not limited to, a hard disc drive, an optical disc drive, and/or a flash memory drive. Further, the memory device may be distributed and located at multiple locations.

The communications module 108 retrieves various data and information from the database 46 and sends information to the user computing device 14 via the communications network 18 to enable the user to access and interact with the system 10. In one embodiment, the communications module 108 displays various images on a graphical interface of the user computing device 14 preferably by using computer graphics and image data stored in the database 46 including, but not limited to, web pages, pharmacy records, in-store on-line records, pharmacy notification messages, in-store on-line notification messages, product lists, and/or any suitable information and/or images that enable the system 10 to function as described herein.

The website hosting module 110 may be programmed to perform some or all of the functions of the website hosting server 36 including hosting various web pages associated with one or more websites that are stored in the database 46 and that are accessible to the user via the user computing device 14. The website hosting module 110 may be programmed to generate and display web pages associated with a website in response to requests being received from users via corresponding web browsers.

The pharmacy account module 112 may be programmed to perform some or all of the functions of the pharmacy account server 40 including monitoring activities associated with pharmacy customers including consumer purchase and/or proscription refill requests, generate notification messages associated with the monitored activities, transmit and received data from $3^{rd}$ party entity server systems 16, and executing verification and authorization operations.

The on-line account module 114 may be programmed to perform some or all of the functions of the on-line account server 42 including monitoring activities associated with in-store on-line customers including consumer purchases and/or product order requests, generate notification messages associated with the monitored activities, transmit and received data from $3^{rd}$ party entity server systems 16, and executing verification and authorization operations.

Other features of the system 10 can be found in the following commonly owned US Patent Applications, which are hereby incorporated by reference: U.S. patent application Ser. No. 15/009,327, filed on Jan. 28, 2016; U.S. patent application Ser. No. 15/009,374, filed on Jan. 28, 2016; U.S. patent application Ser. No. 15/009,417, filed on Jan. 28, 2016; U.S. patent application Ser. No. 15/009,436, filed on Jan. 28, 2016; U.S. patent application Ser. No. 15/009,654, filed on Jan. 28, 2016; U.S. patent application Ser. No. 15/009,583, filed on Jan. 28, 2016; U.S. patent application Ser. No. 15/009,454, filed on Jan. 28, 2016; U.S. patent application Ser. No. 15/009,598, filed on Jan. 28, 2016; U.S. patent application Ser. No. 15/009,611, filed on Jan. 28, 2016; U.S. patent application Ser. No. 15/009,634, filed on Jan. 28, 2016; and, U.S. patent application Ser. No. 15/009, 644, filed on Jan. 28, 2016.

Figure 6:
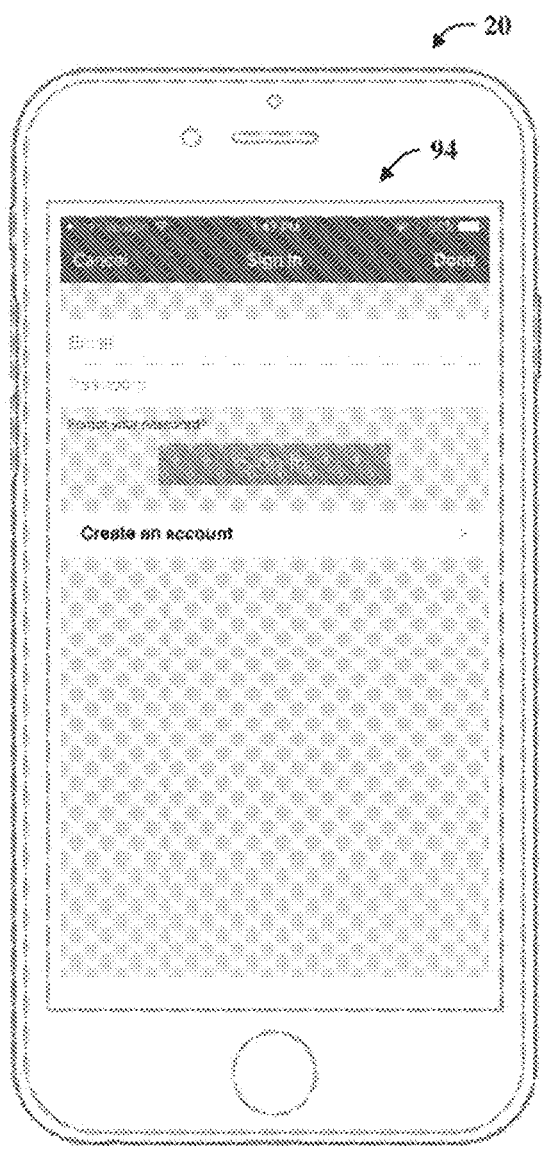
FIGS. 6-9 are illustrations of exemplary screenshots from the system of FIG. 1, according to an embodiment of the present invention.
Figure 7:
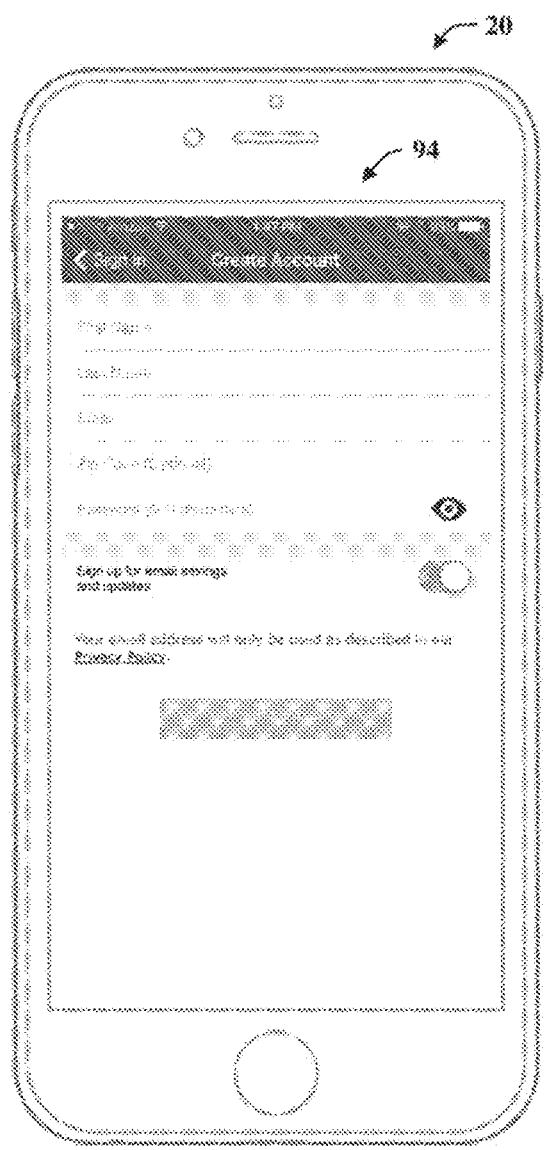
Figure 8:
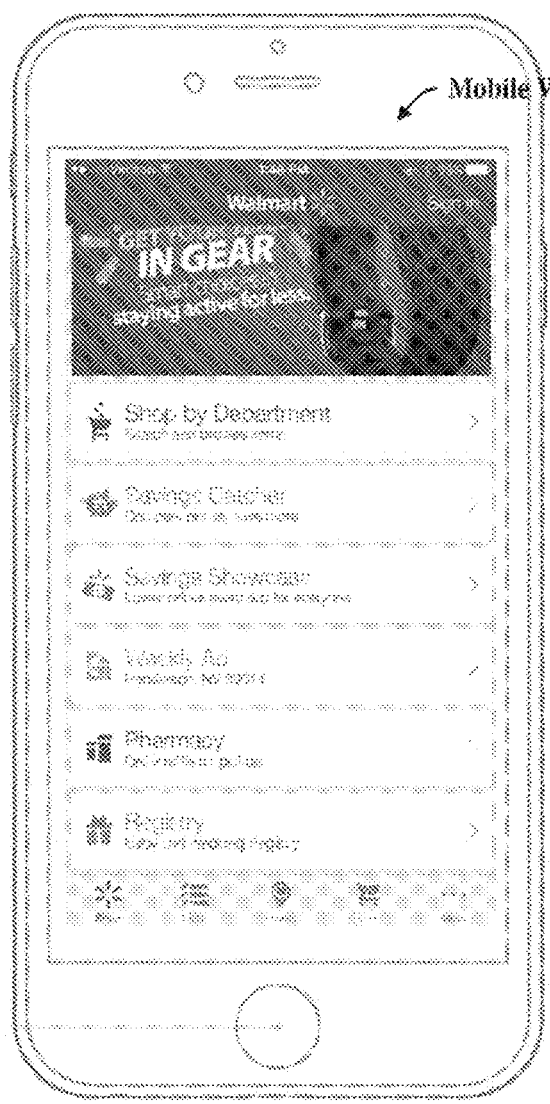
Figure 9:
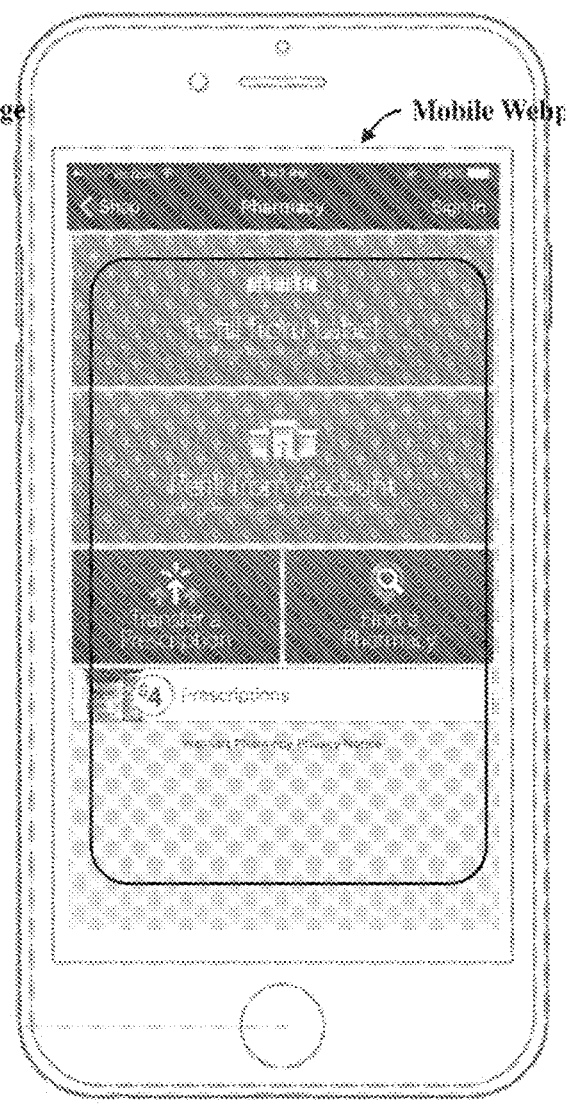
Figure 10:
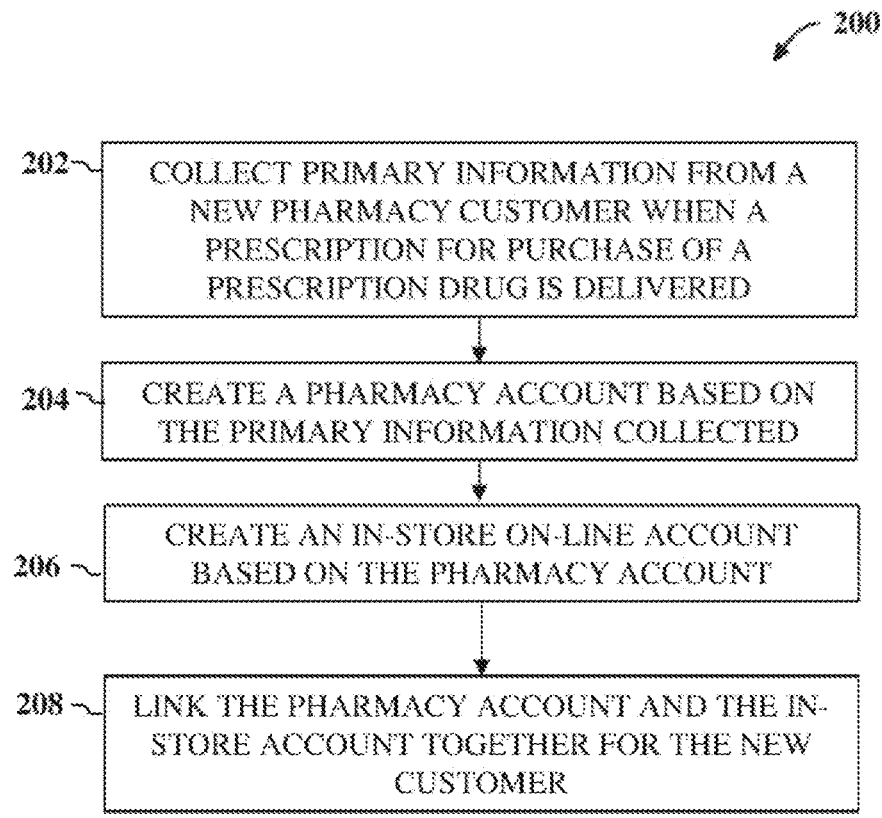
FIG. 10 is a flowchart of a method that may be used with the system shown in FIG. 1, according to embodiments of the present invention.

FIG. 10 is a flowchart of a method 200 that may be used with the system 10 for creating an online account for pharmacy customers. The method includes a plurality of steps. Each method step may be performed independently of, or in combination with, other method steps. Portions of the methods may be performed by any one of, or any combination of, the components of the system 10. FIGS. 6 and 7 are exemplary graphical displays that may be displayed by the system 10.

In the illustrated embodiment, in method step 202, the pharmacy account server 40 collects primary information from a new customer when a prescription for purchase of a prescription drug is delivered by the customer. For example, in one embodiment, the new customer physically delivers the at least one prescription fill order to the pharmacy of the retail store. For example, in another embodiment, the new customer or a physician electronically delivers the at least one prescription fill order to the pharmacy of the retail store. In one embodiment, the pharmacy account server 40 may capture primary information from the new customer. In one embodiment, the primary information is an email address from the new customer. For example, in one embodiment, when a customer goes to pick-up pharmacy medication such as a prescription, the pharmacist or another person behind a counter in the pharmacy of the retail store may capture an e-mail address form the new customer and, once the primary information is captured, the system 12 creates or generates a pharmacy account and an on-line account for the pharmacy customer at the moment when the pharmacy account is created or generated and automatically links the on-line account with the pharmacy account. For example, in another embodiment, when the at least one prescription fill order is delivered electronically to the pharmacy of the retail store, the pharmacist or another person or the system 12 may capture an e-mail address form the new customer and, once the primary information is captured, the system 12 creates or generates a pharmacy account and an on-line account for the pharmacy customer at the moment when the pharmacy account is created or generated and automatically links the on-line account with the pharmacy account. It should be appreciated that this allows the pharmacy customer to obtain pharmacy items as well as other items in the retail store.

In another embodiment, the pharmacy account server 40 may capture secondary information from the new customer. In one embodiment, the secondary information is a type of secondary authentication from the new customer. For example, the secondary authentication may require the customer to enter their birthdate. For example, the pharmacist or another person behind a counter in the pharmacy of the retail store may capture secondary information such as a birthdate in addition to an e-mail address for authentication purposes. For example, the customer may be required to enter their birthdate in addition to their e-mail address for authentication purposes. It should be appreciated that the secondary information may be any suitable type of information for authentication of the customer.

In method step 204, the pharmacy account server 40 creates or generates a pharmacy account based on the primary information collected from the new customer when a prescription for purchase of a prescription drug is delivered by the customer. For example, the system 12 creates or generates a pharmacy account record that is stored in the database 48.

In method step 212, the pharmacy account server 40 creates or generates an on-line account for the new customer based on the pharmacy account for the new customer. For example, the system 12 creates or generates an on-line account record that is stored in the database 48. In one embodiment, the computer computing device 14 or mobile computing device 20 is used to access a web site of the retailer to enter the e-mail address of the new customer and automatically obtain the on-line account. For example, the new customer on their mobile computing device 20 enters their email address in a website running on the mobile computer application running on their mobile computing device 20 to automatically obtain the on-line account of the retailer.

In method step 214, the pharmacy account server 40 links the pharmacy account and the on-line account together for the new customer. In one embodiment, the pharmacy account and the on-line account are linked automatically. In one embodiment, the method includes using one login ID and one password to access the pharmacy account and the on-line account by the customer. In one embodiment, the database 48 includes a plurality of pharmacy account records and a plurality of on-line account records associated with a plurality of customers, each pharmacy account record and each on-line account record including information about one of the customers. The method includes using an email address of the customer to automatically link the pharmacy account and the on-line account together. In one embodiment, the method uses an email address of the customer to automatically link the pharmacy account with an existing on-line account together. For example, the system 12 automatically links the pharmacy account and the on-line account together for the new customer by matching the pharmacy account record and the on-line account record in the database 48 via the e-mail address. It should be appreciated that the records of the database 48 are searched by the database server 46 to link the account records of the customer.

Figure 11A:
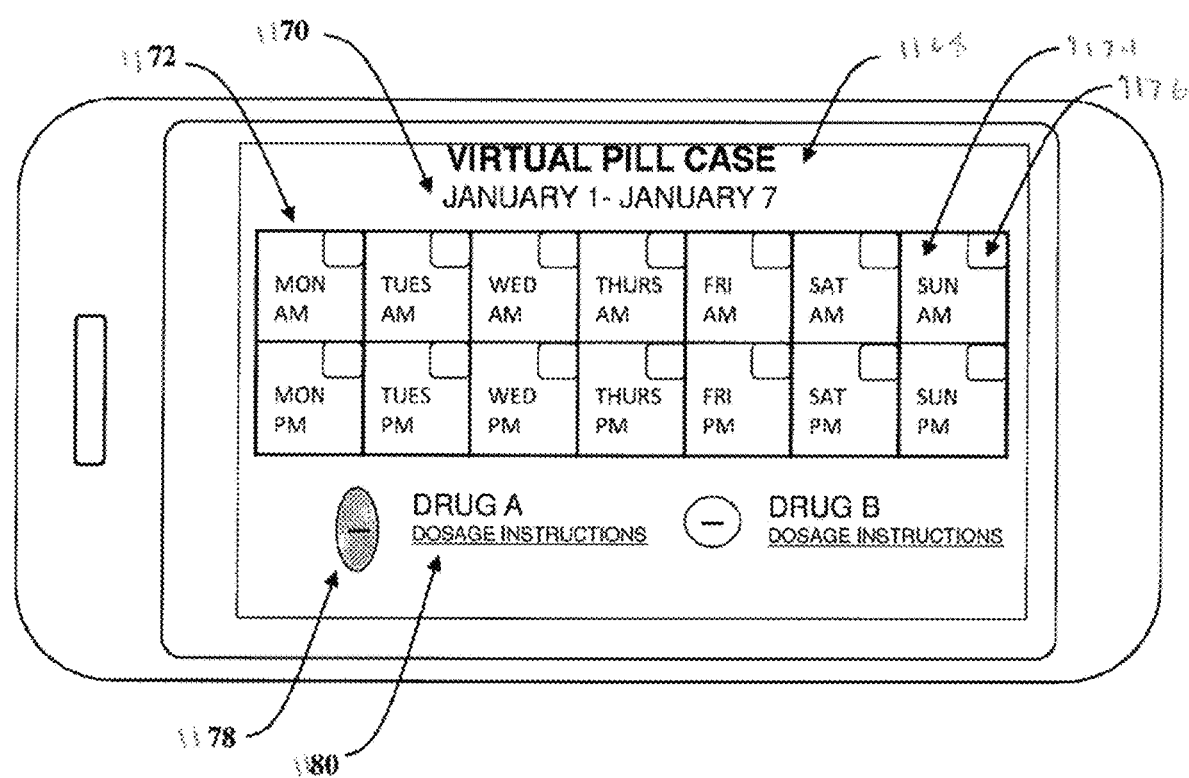
FIGS. 11-12 are illustrations of exemplary screenshots from the system of FIG. 1, according to an embodiment of the present invention.

Referring now to FIG. 11A, the pharmacy account server 40 may store the retrieved information about the prescribed pharmaceutical drug and the prescription information in a virtual pill case 1168 associated with the pharmacy customer. The virtual pill case 1168 may display a date range 1170. The date range 1170 may correspond to a calendar 1172, which may have a separate entry 1174 for each day of the week and, in some cases, entries for different times of day (e.g., AM and PM), similar to a traditional physical pill case. Each entry 1174 may have a checkbox 1176 to indicate whether the pharmacy customer has taken the prescribed dose for that day and/or time. An image 1178 showing the pill associated with the pharmaceutical drug may also be displayed, along with a hyperlink 1180 to additional information about the pharmaceutical drug including dosage instructions. All currently prescribed pharmaceutical drugs stored in database 46 and associated with the customer ID of the pharmacy customer will be shown in the virtual pill case 1168 (e.g., DRUG A and DRUG B).

Figure 11B:
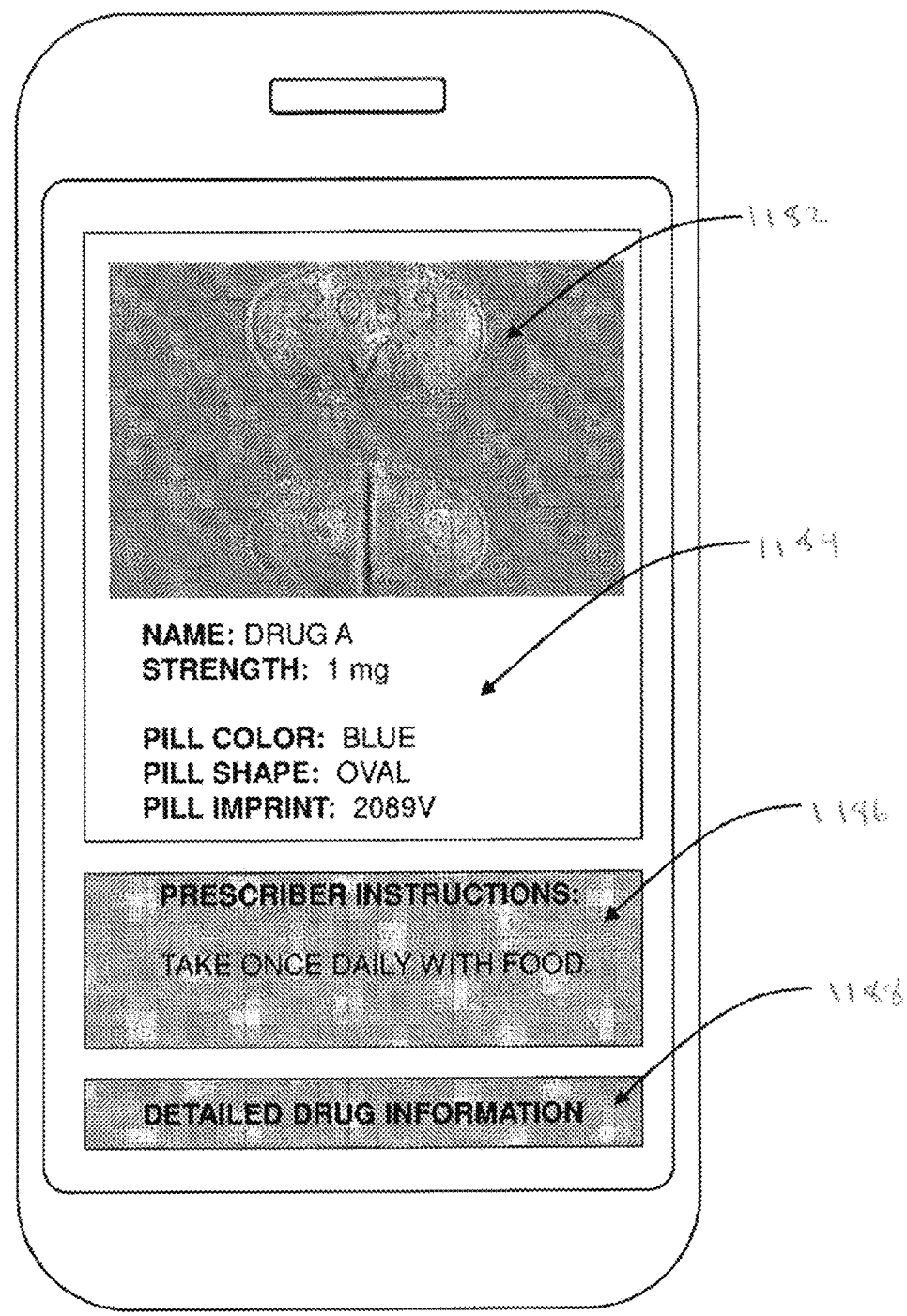

Referring now to FIG. 11B, when the pharmacy customer follows hyperlink 1180, the additional information about the pharmaceutical drug is displayed. In the illustrated embodiment, a photograph 1182 shows the pill (or other medication administration device) associated with the pharmaceutical drug. Drug details 1184 include, for example, the name, class, and strength of the drug, as well as the shape, color, and imprint of the pill. Additionally, dosage instructions 1186 are displayed, which include personalized instructions for administration of the medication as prescribed for the pharmacy customer. The pharmacy customer may access additional information via a hyperlink 1188, which may take the pharmacy customer to a third party website and display, for instance, information about side effects and drug and food interactions associated with the pharmaceutical drug.

Figure 11C:
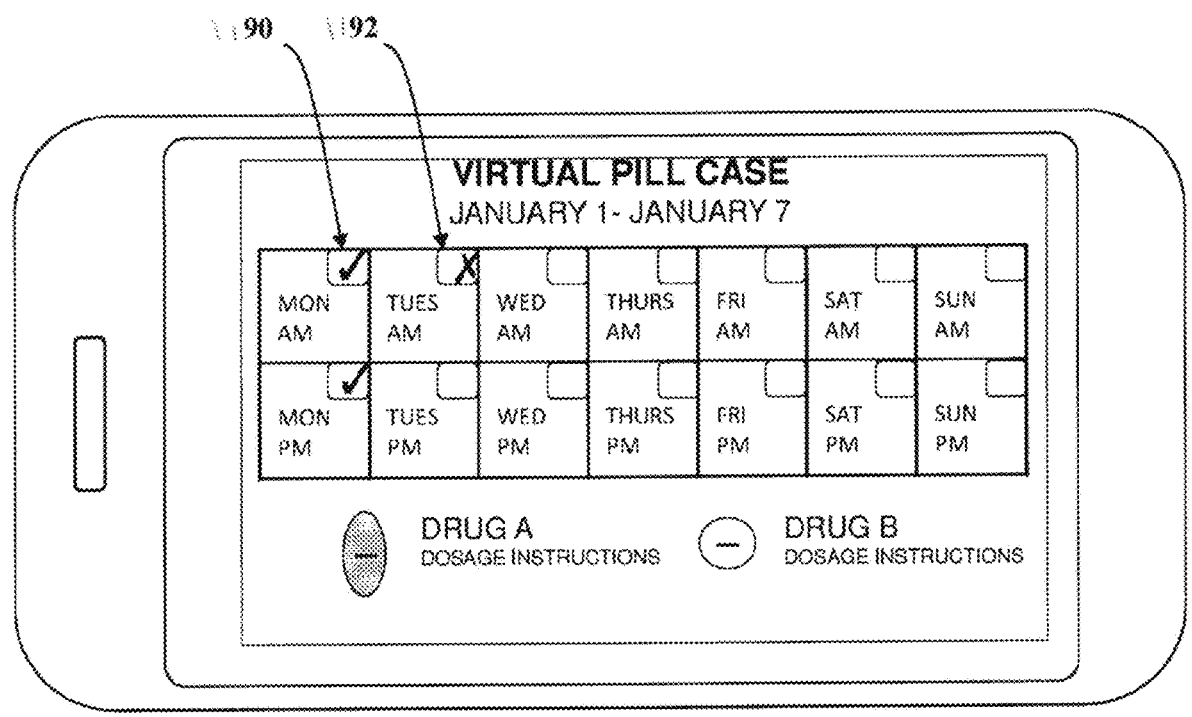

Referring now to FIG. 11C, the pharmacy customer may indicate that a dosage was taken by placing a taken dose symbol 1190. If the pharmacy customer misses a dose, a missed dose symbol 1192 may be shown. In response to a missed dose, a pharmacy notification may be sent to the pharmacy customer.

Figure 12:
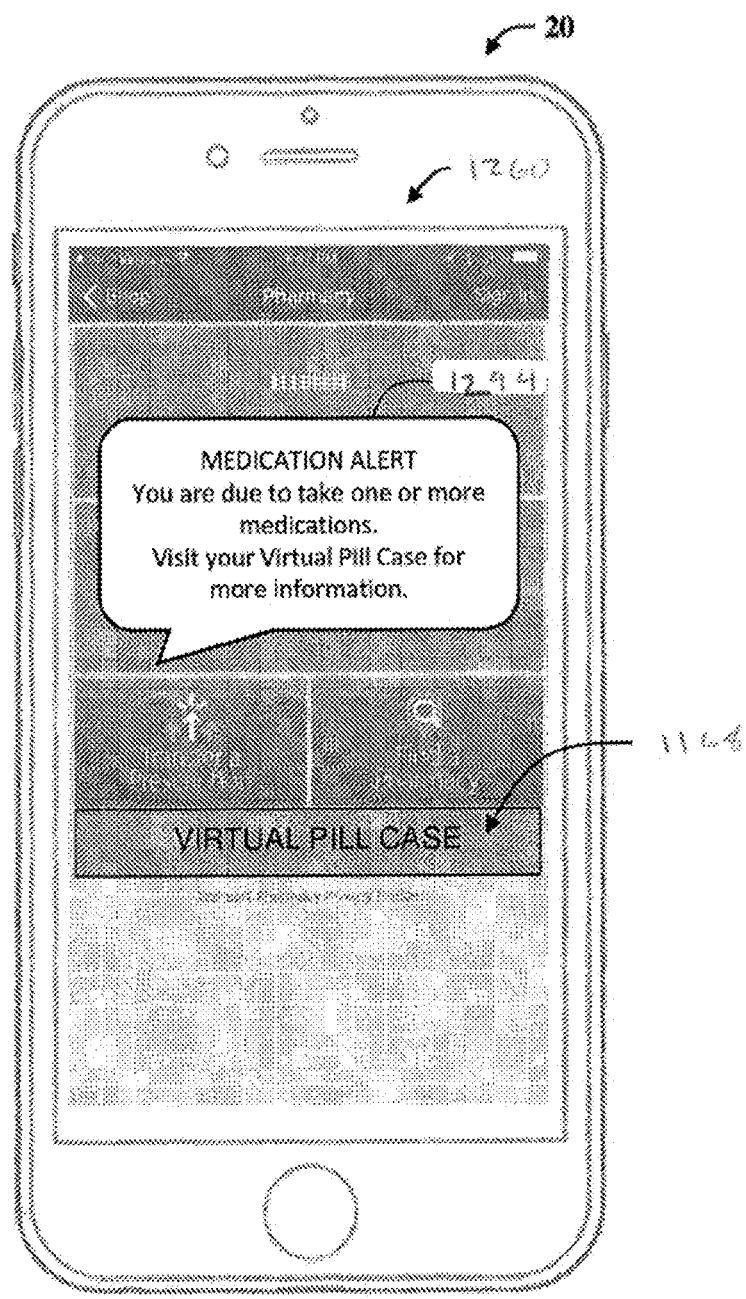

Referring now to FIG. 12, in one embodiment, the pharmacy account server 40 may receive a request to display a pharmacy notification message 1294 to the pharmacy customer via a user computing device 14. In one embodiment, the pharmacy account server 40 may receive a request to display the pharmacy notification message on a mobile computing device 20. The request may include a corresponding user ID. Upon receiving the request, the pharmacy account server 40 accesses the database 46 and identifies a user pharmacy account record 50 associated with the received user ID. The pharmacy account server 40 detects an occurrence of a triggering event as a function of the triggering event data, such as a missed dose by the pharmacy customer, and generates the pharmacy notification message 1294. The pharmacy account server 40 then generates and transmits a signal including the pharmacy notification message to the mobile computing device 20 to cause the mobile computing device 20 to display the pharmacy notification message on the mobile computing device 20.

FIGS. 13-16 are flowcharts of methods 1300, 1400, 1500, and 1600 that may be used with the system 10 for monitoring activities of pharmacy customers and generating and displaying information to the pharmacy customers on a website via a mobile computing device. The methods include a plurality of steps. Each method step may be performed independently of, or in combination with, other method steps. Portions of the methods may be performed by any one of, or any combination of, the components of the system 10.

Figure 13:
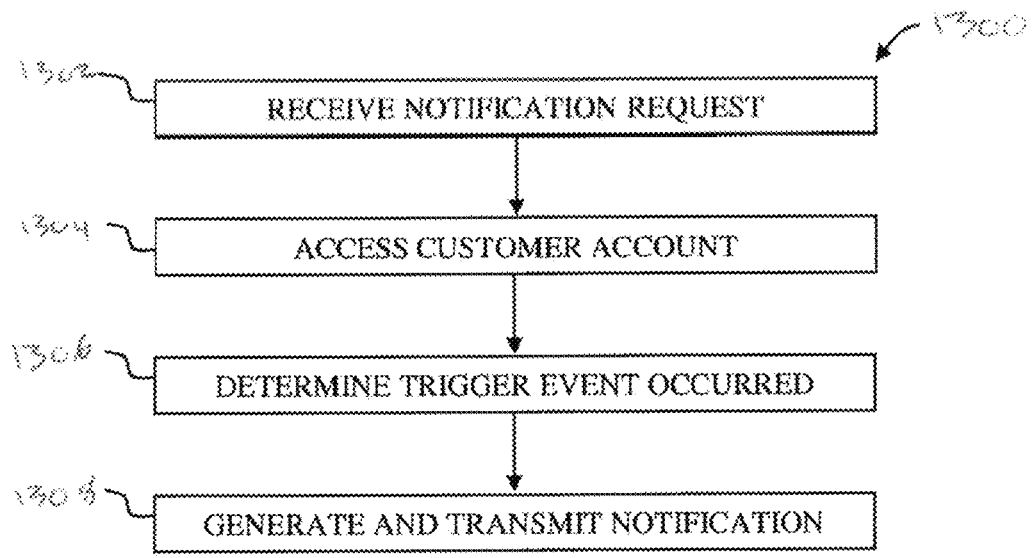
FIGS. 13-16 are flowcharts of methods that may be used with the system shown in FIG. 1, according to embodiments of the present invention.

Referring now to FIG. 13, a method 1300 for determining new prescription information is available is shown. At step 1302, the pharmacy account server 40 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 40 may be programmed to initiate a notification operation at a specific time and/or upon receiving an indication of activities associated with a pharmacy customer.

At step 1304, the pharmacy account server 40 accesses the user pharmacy account list 48 being stored in the database 46 to determine a user pharmacy account record 50 associated with the received user ID.

At step 1306, the pharmacy account server 40 determines that a triggering event has occurred. For example, in one embodiment, the triggering event may include a purchase of a new prescription by the pharmacy customer associated with the user ID. In another embodiment, the triggering event may include an indication that a pharmaceutical drug associated with the user ID requires a refill.

At step 1308, the pharmacy account server 40 generates and transmits a pharmacy notification message to the pharmacy customer requesting that the pharmacy customer add the new prescription information to the pharmacy customer's virtual pill case 1168. In the illustrated embodiment, the pharmacy account server 40 generates and transmits a signal including the notification message to the mobile computing device 20 to cause the mobile computing device 20 to display the notification message on the mobile computing device 20. For example, the pharmacy account server 40 may generate a notification upon detecting a new prescription or new refill. In one embodiment, the system 10 may access the corresponding user pharmacy account records 50 to determine a messaging API associated with an operating system of the mobile computing device 20 and generate the notification message as a function of the retrieved messaging API to enable the mobile computing device 20 to display the received message. In one embodiment, each user account record includes information associated with the mobile computing device 20 including a unique mobile ID and message API. In another embodiment, the user pharmacy account records 50 may include a message preferences, such as, for example, an email, text message, push messaging, automated phone call, and the like. The pharmacy account server 40 identifies the messaging preference associated with the user pharmacy account records 50 and generates the notification message based on the message preference.

Figure 14:
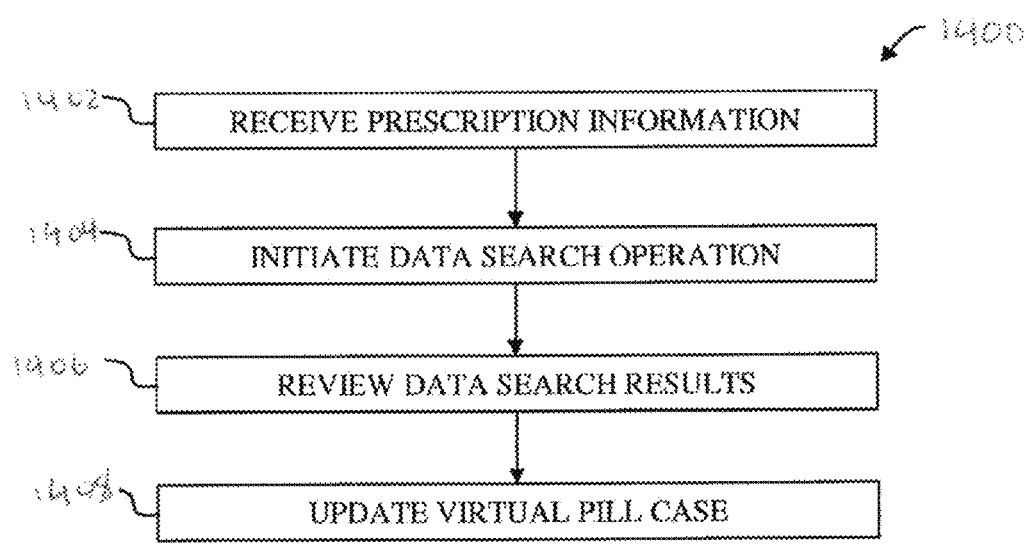

Referring now to FIG. 14, a method 1400 for acquiring new prescription information is shown. At step 1402, prescription information is received (e.g., manually entered by the pharmacy customer or received via an electronic transaction record).

At step 1404, the pharmacy account server 40 initiates a data search operation including transmitting the prescription information to a search engine server. In one embodiment, during the data search operation, the pharmacy account server 40 generates search terms associated with a prescribed pharmaceutical drug included in the identified user pharmacy account record 50 and transmits the search terms to the search engine server. The search engine server may initiate a search on the $3^{rd}$ party entity server system 16. The search results may be transmitted from the search engine server to the pharmacy account server 40. The search results may include information about the pharmaceutical drug, including information about the pill shape, size, color, and strength, and an image or photograph representing the pill (or inhaler, pump, patch, or other device by which the pharmaceutical drug is administered).

At step 1406, the pharmacy account server 40 reviews the data search results and determines whether new information not already stored in the virtual pill case has been retrieved. For example, the prescription information may correspond to a refill of a pharmaceutical drug that is already stored in the pharmacy customer's virtual pill case, but the search results may indicate new information is available for the pharmaceutical drug because the manufacturer has changed the pill shape since the pharmacy customer's previous refill.

At step 1408, the virtual pill case is updated with any new information retrieved via the search results.

Figure 15:
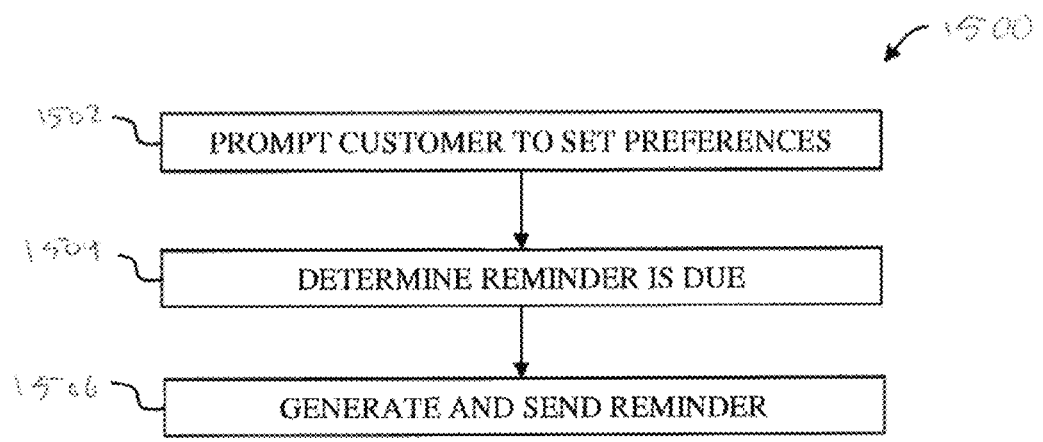

Referring now to FIG. 15, a method 1500 for sending a reminder to pharmacy customer regarding a virtual pill case. At step 1502, the pharmacy account server 40 prompts a pharmacy customer to set one or more reminder preferences regarding a virtual pill case. Reminder preferences may include, for example, whether the customer wishes to receive reminders regarding the virtual pill case. If the customer wishes to receive reminders, the customer may indicate a frequency with which the reminder should be sent (e.g., daily, weekly, etc.) and when the reminder should be sent (e.g., in the morning, afternoon, or evening, or at a specific time). The user may also indicate whether the reminder should be sent only if the user has missed a scheduled medication dose, or if the reminder should always be sent. Additionally, the user may indicate the preferred method of transmission of the reminder (e.g., push notification, text message, e-mail, etc.).

At step 1504, the pharmacy account server 40 determines that a reminder to the pharmacy customer is due, based on the customer's set reminder preferences. At step 1506, the pharmacy account server 40 generates and sends a reminder to the pharmacy customer regarding the virtual pill case.

Figure 16:
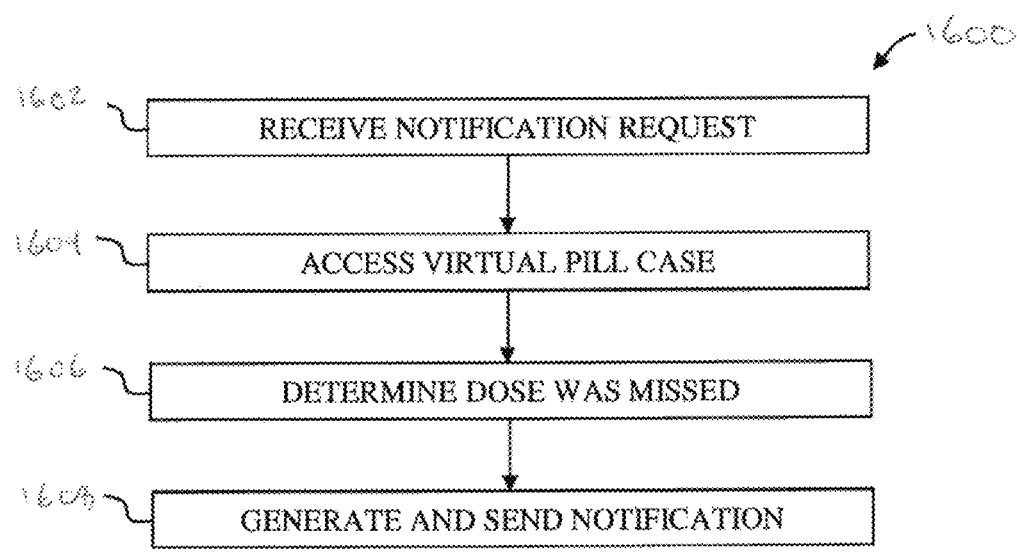

Referring now to FIG. 16, a method 1600 for sending a missed dose notification to pharmacy customer using a virtual pill case. At step 1602, the pharmacy account server 40 receives a request to initiate a notification operation to monitor an activity of a pharmacy customer. The request includes a corresponding user ID. In one embodiment, the request may be received from a mobile computing device 20 associated with a pharmacy customer. In another embodiment, the request may be initiated by the customer via the pharmacy website. In addition, the pharmacy account server 40 may be programmed to initiate a notification operation at a specific time and/or upon receiving an indication of activities associated with a pharmacy customer.

At step 1604, the pharmacy account server 40 accesses a virtual pill case associated with the pharmacy customer. At step 1606, the pharmacy account server 40 determines that the pharmacy customer missed at least one scheduled dose of a pharmaceutical drug according to dosage instructions provided by a prescriber. At step 1608, the pharmacy account server 40 generates and sends a notification to the pharmacy customer regarding the missed dose and prompting the user to visit the virtual pill case to review dosage instructions.

A controller, computing device, server or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention.

What is claimed is:

1. A system comprising:
a server including a processor programmed to:
create a purchase history for a new customer by monitoring purchase activity of the new customer (1) on a website of an eCommerce retailer and (2) in a brick and mortar store of the eCommerce retailer;
determine, based on the purchase activity of the new customer, when a prescription for purchase of a prescription drug for the new customer was delivered to the brick and mortar store of the eCommerce retailer;
in response to determining when the prescription was delivered, automatically create a pharmacy account based on primary information collected from (1) the purchase history of the new customer on the website of the eCommerce retailer, (2) the purchase history of the new customer in the brick and mortar store of the eCommerce retailer, and (3) the prescription;

automatically link the pharmacy account with an on-line account for the new customer on the website of the eCommerce retailer using the primary information;

receive, from an electronic device of the new customer, a login request for the pharmacy account, the login request comprising login information;

authenticate the login information;

transmit (1) the purchase history of the new customer on the website of the eCommerce retailer, (2) the purchase history of the new customer in the brick and mortar store of the eCommerce retailer, and (3) the prescription to a third party entity server configured to provide additional medical services for the new customer; and transmit instructions to display, on the electronic device of the new customer, a virtual pill case including:
  a date range;
  first prescription information about at least one medication, wherein:
    the first prescription information comprises dosage instructions for a pharmaceutical drug of the new customer; and
    the pharmaceutical drug is scheduled to be taken by the new customer during the date range;
  a first image of the pharmaceutical drug;
  a first customized hyperlink; and
  a selectable user interface element corresponding to the pharmaceutical drug.

2. A system as set forth in claim 1 wherein the processor is further programmed to capture the primary information from the new customer.

3. A system as set forth in claim 2 wherein the primary information comprises an email address from the new customer.

4. A system as set forth in claim 1 wherein the processor is further programmed to capture secondary information from the new customer.

5. A system as set forth in claim 4 wherein the secondary information comprises a type of secondary authentication from the new customer.

6. A system as set forth in claim 1 wherein the pharmacy account and the on-line account are linked automatically.

7. A system as set forth in claim 3 wherein the electronic device of the new customer is configured to:
  access a website to enter the email address of the new customer and automatically obtain the on-line account.

8. A system as set forth in claim 1 wherein the login information comprises one login account identification and one password.

9. A system as set forth in claim 1 including a database including a plurality of pharmacy account records and a plurality of on-line account records associated with a plurality of customers, each respective pharmacy account record of the plurality of pharmacy account records and each respective on-line account record of the plurality of on-line account records including respective information about one respective customer of the plurality of customers.

10. A system as set forth in claim 1 including using an email address to automatically link the pharmacy account and an existing on-line account together.

11. A method comprising steps of:
creating a purchase history for a new customer by monitoring purchase activity of the new customer (1) on a website of an eCommerce retailer and (2) in a brick and mortar store of the eCommerce retailer;

determining, based on the purchase activity of the new customer, when a prescription for purchase of a prescription drug for the new customer was delivered to the brick and mortar store of the eCommerce retailer;

in response to determining when the prescription was delivered, automatically creating a pharmacy account based on primary information collected from (1) the purchase history of the new customer on the website of the eCommerce retailer, (2) the purchase history of the new customer in the brick and mortar store of the eCommerce retailer, and (3) the prescription;

automatically linking the pharmacy account with an on-line account for the new customer on the website of the eCommerce retailer using the primary information;

receiving, from an electronic device of the new customer, a login request for the pharmacy account, the login request comprising login information;

authenticating the login information;

transmitting (1) the purchase history of the new customer on the website of the eCommerce retailer, (2) the purchase history of the new customer in the brick and mortar store of the eCommerce retailer, and (3) the prescription to a third party entity server configured to provide additional medical services for the new customer; and transmitting instructions to display, on the electronic device of the new customer, a virtual pill case including:
  a date range;
  first prescription information about at least one medication, wherein:
    the first prescription information comprises dosage instructions for a pharmaceutical drug of the new customer; and
    the pharmaceutical drug is scheduled to be taken by the new customer during the date range;
  a first image of the pharmaceutical drug;
  a first customized hyperlink; and
  a selectable user interface element corresponding to the pharmaceutical drug.

12. A method as set forth in claim 11 including a step of capturing the primary information from the new customer.

13. A method as set forth in claim 12 wherein the primary information comprises an email address from the new customer.

14. A method as set forth in claim 11 including a step of capturing secondary information from the new customer.

15. A method as set forth in claim 14 wherein the secondary information comprises a type of secondary authentication from the new customer.

16. A method as set forth in claim 11 including a step of linking automatically the pharmacy account and the on-line account.

17. A method as set forth in claim 13 wherein the electronic device of the new customer is configured to:
  access a website to enter the email address of the new customer and automatically obtain the on-line account.

18. A method as set forth in claim 11 wherein the login information comprises one login account information and one password.

19. A method as set forth in claim 11 including providing a database including a plurality of customer pharmacy account records and a plurality of on-line account records associated with a plurality of customers, each respective customer pharmacy account record of the plurality of customer pharmacy account records and each respective on-line account record of the plurality of on-line account records including respective information about one respective customer of the plurality of customers.

20. A method as set forth in claim 11 including using an email address to automatically link the pharmacy account and an existing on-line account together.

21. One or more non-transitory computer-readable storage media, having computer-executable instructions embodied thereon, wherein when executed by at least one processor, the computer-executable instructions cause the processor to:
- create a purchase history for a new customer by monitoring purchase activity of the new customer (1) on a web site of an eCommerce retailer and (2) in a brick and mortar store of the eCommerce retailer;
- determine, based on the purchase activity of the new customer, when a prescription for purchase of a prescription drug for the new customer was delivered to the brick and mortar store of the eCommerce retailer;
- in response to determining when the prescription was delivered, automatically create a pharmacy account based on primary information collected from (1) the purchase history of the new customer on the website of the eCommerce retailer, (2) the purchase history of the new customer in the brick and mortar store of the eCommerce retailer, and (3) the prescription;
- automatically link the pharmacy account with an on-line account for the new customer on the website of the eCommerce retailer using the primary information;
- receive, from an electronic device of the new customer, a login request for the pharmacy account, the login request comprising login information;
- authenticate the login information;
- transmit (1) the purchase history of the new customer on the website of the eCommerce retailer, (2) the purchase history of the new customer in the brick and mortar store of the eCommerce retailer, and (3) the prescription to a third party entity server configured to provide additional medical services for the new customer; and
- transmit instructions to display, on the electronic device of the new customer, a virtual pill case including:
  - a date range;
  - first prescription information about at least one medication, wherein:
    - the first prescription information comprises dosage instructions for a pharmaceutical drug of the new customer; and
    - the pharmaceutical drug is scheduled to be taken by the new customer during the date range;
  - a first image of the pharmaceutical drug;
  - a first customized hyperlink; and
  - a selectable user interface element corresponding to the pharmaceutical drug.

\* \* \* \* \*